United States Patent
Zeko et al.

(10) Patent No.: US 9,784,720 B2
(45) Date of Patent: Oct. 10, 2017

(54) QUICK LOCK CONNECTOR FOR CONNECTING A CAPILLARY TO A FLUIDIC CONDUIT OF A FLUIDIC COMPONENT

(75) Inventors: Darijo Zeko, Waldbronn (DE); Jose-Angel Mora-Fillat, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 368 days.

(21) Appl. No.: 14/376,386

(22) PCT Filed: Feb. 1, 2012

(86) PCT No.: PCT/EP2012/051710
§ 371 (c)(1),
(2), (4) Date: Aug. 1, 2014

(87) PCT Pub. No.: WO2013/113386
PCT Pub. Date: Aug. 8, 2013

(65) Prior Publication Data
US 2014/0375050 A1     Dec. 25, 2014

(51) Int. Cl.
*F16L 37/00* (2006.01)
*G01N 30/60* (2006.01)
*F16L 37/08* (2006.01)

(52) U.S. Cl.
CPC .......... *G01N 30/6004* (2013.01); *F16L 37/08* (2013.01); *G01N 30/6039* (2013.01)

(58) Field of Classification Search
USPC ............................ 285/342, 312, 394, 38, 358
See application file for complete search history.

(56) References Cited

U.S. PATENT DOCUMENTS 2,444,414 A * 7/1948 Anderson ............... F16L 37/12
                                                                251/149.6
3,738,688 A * 6/1973 Racine .................... F16L 37/05
                                                                285/179

(Continued)

FOREIGN PATENT DOCUMENTS

WO           9215426          9/1992

OTHER PUBLICATIONS

International Search Report mailed Oct. 22, 2012 for Application No. PCT/EP2012/051710.

(Continued)

*Primary Examiner* — Aaron Dunwoody

(57) ABSTRACT

A fitting for providing a fluid connection between a capillary and a fluidic conduit of a fluidic component, wherein the fitting comprises a capillary reception configured for receiving the capillary, a force applicator configured for being operable to apply a fixing force for fixing the capillary within the fitting, a force limitation mechanism configured for limiting the fixing force being applicable by the force applicator to the capillary, a force splitter configured for splitting the fixing force into an advance force component for advancing the capillary received in the capillary reception towards the fluidic component and into a clamping force component for clamping the capillary received in the capillary reception within the fitting, and a biasing mechanism particularly arranged between the force applicator and the force splitter and configured for biasing the force splitter against the capillary.

18 Claims, 3 Drawing Sheets

(56) References Cited

U.S. PATENT DOCUMENTS

| | | | | |
|---|---|---|---|---|
| 3,779,587 A * | 12/1973 | Racine | ............... | F16L 37/18 |
| | | | | 285/179 |
| 3,868,132 A * | 2/1975 | Racine | ............... | F16L 37/18 |
| | | | | 138/89 |
| 3,973,792 A | 8/1976 | Gonner | | |
| 4,225,159 A * | 9/1980 | Van Meter | .......... | F16L 55/132 |
| | | | | 285/104 |
| 4,254,801 A * | 3/1981 | Gerthoffer | ......... | F16L 55/1157 |
| | | | | 138/89 |
| 4,326,407 A * | 4/1982 | Van Meter | .......... | G01M 3/022 |
| | | | | 285/102 |
| 4,991,883 A * | 2/1991 | Worden | ............ | B01J 4/001 |
| | | | | 285/334.4 |
| 5,163,722 A * | 11/1992 | Worden | ............ | F16L 37/242 |
| | | | | 285/101 |
| 5,215,340 A * | 6/1993 | Ledford, Jr. | ........... | F16L 37/00 |
| | | | | 285/312 |
| 5,234,235 A * | 8/1993 | Worden | ............ | F16L 29/04 |
| | | | | 285/334.4 |
| 5,507,537 A * | 4/1996 | Meisinger | ........... | F16L 37/05 |
| | | | | 285/312 |
| 5,575,510 A * | 11/1996 | Weh | ............... | F16L 37/1215 |
| | | | | 285/312 |
| 5,788,290 A * | 8/1998 | Meisinger | .......... | F16L 37/1215 |
| | | | | 137/614.06 |
| 6,099,044 A * | 8/2000 | Weh | ............... | F16L 37/1215 |
| | | | | 285/312 |
| 6,102,449 A * | 8/2000 | Welsh | ............. | F16L 19/07 |
| | | | | 285/332 |
| 6,155,611 A * | 12/2000 | Lemire | ............ | F16L 37/18 |
| | | | | 285/312 |
| 6,193,286 B1 * | 2/2001 | Jones | ............... | G01N 30/6004 |
| | | | | 285/343 |
| 6,494,500 B1 * | 12/2002 | Todosiev | .......... | G01N 30/6026 |
| | | | | 285/279 |
| 7,735,878 B2 * | 6/2010 | Keene | ............. | F16L 15/009 |
| | | | | 285/332 |
| 8,696,902 B2 * | 4/2014 | Ford | ............... | G01N 30/6039 |
| | | | | 210/198.2 |
| 2005/0284213 A1 | 12/2005 | Karp et al. | | |
| 2008/0038152 A1 | 2/2008 | Pelt | | |
| 2010/0224543 A1 | 9/2010 | Ellis et al. | | |
| 2011/0303593 A1 | 12/2011 | Reinhardt | | |

OTHER PUBLICATIONS

Chinese Office action dated Mar. 25, 2016 from related Chinese Application No. 201280068908.5.
International Search Report and Written Opinion mailed Oct. 22, 2012 for Application No. PCT/EP2012/051710.
Office Action mailed Jul. 22, 2015 in Chinese Application No. 201280068908.5 (Unofficial/non-certified translation provided by foreign agent included).

* cited by examiner

QUICK LOCK CONNECTOR FOR CONNECTING A CAPILLARY TO A FLUIDIC CONDUIT OF A FLUIDIC COMPONENT

The present application is a national stage application under 35 U.S.C. §371 and claims priority under 35 U.S.C. §121 from International Patent Application No. PCT/EP2012/051710 filed on Feb. 1, 2012. The entire disclosure of International Patent Application No. PCT/EP2012/051710 is specifically incorporated herein by reference.

BACKGROUND ART

The present invention relates to fluidically coupling fluidic components, in particular in a high performance liquid chromatography application.

In liquid chromatography, a fluidic sample (mobile phase) may be pumped through conduits and a column comprising a material (stationary phase) which is capable of separating different components of the fluidic analyte. Such a material, so-called beads which may comprise silica gel, may be filled into a column tube which may be connected to other elements (like a sampling unit, a flow cell, containers including sample and/or buffers) by conduits.

The flow path of the mobile phase typically comprises plural individual components coupled together, which, in turn, might also be comprised of individual sub-components. Due to the high pressure applied in most HPLC application, pressure sealing of the components in and along the flow path is required. Further, in case of requirement of biocompatibility, it has to be ensured that all surfaces of components (including conduits) along the flow path, which may come in contact with the mobile phase and the sample fluid, are comprised of materials generally considered as being biocompatible, i.e. not to release ions (e.g. from metal parts) which may contaminate the sample and/or a column packaging material, and/or adversely affect the analysis itself. Accordingly, proper sealing is required to ensure such biocompatibility. Sealings should also provide for a small dead volume and low carryover.

A so called fitting is a fluidic component being capable of providing a sealed connection between a capillary and another fluidic conduit (such as another capillary or a channel in a substrate or the like).

U.S. Pat. No. 3,973,792 discloses that, in a connecting device for connecting chromatographic separating columns of glass to terminal fittings on a chromatographic apparatus, each end of the column is surrounded by a metallic sleeve. A sleeve made of synthetic plastic material, which is of substantially stable shape at least up to a temperature of 350° centigrade even if subjected to pressure, is interposed between said end and said metallic sleeve. The plastic sleeve has at least one conical end face and is held in sealing engagement with the end of the separating column, on one hand, and with the metallic sleeve, on the other hand, by a sleeve shaped thrust member, which is axially movable relative to the metallic sleeve to exert an axial force on said plastic sleeve. A radial sealing force is exerted on the synthetic plastic sleeve through its conical end face by an abutting complementary conical surface. Connecting means for gas-tightly and detachably connecting the ends of the column to the terminal fittings of the apparatus are provided on the metallic sleeve.

WO 92/15426 discloses an apparatus and a method for connecting the end of a tubular body, particularly a chromatographic capillary tube, to a detection or injection device fitting. WO 92/15426 provides an apparatus which comprises a holder having a ferrule for holding the tubular body. Connection of the tubular body to a device fitting is aided by an insertion assembly. The insertion assembly is adapted to contain the holder and force the ferrule into a seated relation with the device.

However, the requirements regarding sealing performance and mechanical stability of a fluidic component of fluidic measurement devices increases with further increasing operation pressure values. At the same time, fast and easy handling of such a fitting by a user is required.

DISCLOSURE

It is an object of the invention to provide an efficient sealing fluidic component for a fluidic device which is simple in operation.

According to an exemplary embodiment of the present invention, a fitting for providing a fluid connection between a capillary and a fluidic conduit (such as a further capillary, a fluidic channel in a substrate, etc.) of a fluidic component is provided, wherein the fitting comprises a capillary reception configured for receiving the capillary, a force applicator configured for being operable (particularly by a user) to apply a fixing force for fixing the capillary within the fitting, a force limitation mechanism configured for limiting the fixing force being applicable by the force applicator to the capillary, a force splitter configured for splitting the fixing force into an advance force component (particularly oriented longitudinally along an extension direction of the capillary reception) for advancing the capillary received in the capillary reception (particularly forwardly) towards the fluidic component and into a clamping force component for (particularly circumferentially and/or inwardly) clamping the capillary received in the capillary reception within the fitting, and a biasing mechanism (particularly arranged between the force applicator and the force splitter) configured (particularly mounted within the fitting) for biasing the force splitter against the capillary.

According to another exemplary embodiment, a fluidic device for conducting a fluidic sample is provided, wherein the fluidic device comprises a fluidic component having a fluidic conduit, a capillary, and a fitting having the above mentioned features for providing a fluid connection between the capillary and the fluidic conduit for conducting the fluidic sample through the fluidic device.

According to still another exemplary embodiment, a method of fluidically coupling a capillary with a fluidic conduit of a fluidic component by a fitting is provided, wherein the method comprises receiving the capillary in a capillary reception of the fitting, operating a force applicator of the fitting to apply a fixing force for fixing the capillary within the fitting, limiting the fixing force being applicable by the force applicator to the capillary by a force limitation mechanism of the fitting, splitting the fixing force, by a force splitter of the fitting, into an advance force component for advancing the capillary received in the capillary reception towards the fluidic component and into a clamping force component for clamping the capillary received in the capillary reception within the fitting, and biasing the force splitter against the capillary by a biasing mechanism of the fitting, the biasing mechanism being particularly arranged between the force applicator and the force splitter.

In an embodiment, a fluidic fitting is provided which is configured for coupling a capillary with another fluidic conduit by applying a failure resistant mechanism, operable by a user, for fixing the capillary at the fitting, while at the same time applying a reproducible and predefined fixing force to the capillary. This fixing force can be rendered sufficiently large so as to securely fasten the capillary at the fitting, at the same time a force limitation mechanism prevents an exceeding fixing force which would deteriorate or even destroy the fitting or the capillary. Moreover, a biasing mechanism such as a spring or a spring package may bias the force splitter to apply a certain pressure to the capillary. In a scenario in which, due to temperature or aging effects, the force applied from the force applicator to the capillary becomes too small, the biasing mechanism ensures that in each configuration a sufficient biasing force for sealingly connecting the capillary within the fitting is provided.

In the following, further embodiments of the fitting will be explained. However, these embodiments also apply to the fluidic device and the method.

In an embodiment, the force applicator has a lever operable by a user and an eccentric shaft rigidly coupled to the lever so that pivoting of the lever (starting from an operation mode in which the capillary is in a non-fixed state in the capillary reception) pushes the eccentric shaft towards (i.e. in direction of) the biasing mechanism to thereby apply the fixing force (finishing at an operation mode in which a capillary is in a fixed state in the capillary reception). By providing a lever mechanism it is easy for a user to manually operate the force applicator, since it is sufficient to pivot the lever using the muscle force of the user only to fix the capillary to the fitting.

The force applicator may have a rod like configuration when the lever forms one end of the rod. An opposing end of this rod may be formed by an eccentric shaft, i.e. a shaft around which a pivoting is possible. The eccentric shaft may be mounted in a housing of the fitting. Therefore, rotation of the eccentric shaft triggered by actuating the lever will automatically result in a continuous increase of the force applied towards the capillary, since the thicker end of the eccentric shaft may be pressed increasingly powerful in direction of the biasing mechanism. Hence, the biasing mechanism will transmit a corresponding applied fixing force, merely exerted by pivoting the lever, towards the force splitter.

The skilled person will understand that a lever mechanism is only one possibility for a user operated component suitable for applying the fixing force. As an alternative to the lever based force applicator (with the defined abutment mechanism) it is possible to use a screw in connection with a latch. Still other embodiments may embody the force applicator by a differential thread. Also a hydraulic or a pneumatic force applicator is possible. It is also possible to embody the force applicator by a screw nut in combination with a wrench.

In an embodiment, the force applicator is configured to be manually operable by a user, particularly is configured to be toollessly operable by a user. Such an embodiment has the advantage that no tools or automatic drive mechanism such as a motor is necessary for operating, particularly activating, the capillary fixation. In contrast to this, with a small amount of muscle force only it is possible to reliably fix the capillary to the fitting.

In an embodiment, the force limitation mechanism has a first abutment member forming part of the force applicator and has a second abutment member forming part of a fitting housing. The first abutment member and the second abutment member may be configured so as to abut to one another upon exceeding a predefined degree of actuating the force applicator (for instance upon exceeding a certain rotation angle of a lever) for inhibiting continued operation of the force applicator (which would result in a fixing force exceeding a predefined maximum fixing force) thereby inhibiting or preventing exceeding of the fixing force. When no force is applied to a capillary, i.e. when the force applicator is in an inactive (or non-force applying) state, the first abutment section does not contact the second abutment section. However, upon actuating the force applicator, for instance by rotating a lever of a lever-based force applicator, the first abutment section will be contacted with the second abutment section at a certain point of time during the lever operation. This will have the effect that a further rotation of the lever will not result in a further increased fixing force. Therefore, by a simple mechanical abutment mechanism, it is possible to define a maximum fixing force acting on the capillary. It is not possible that this force is exceeded, since this is prevented by the abutment of the first abutment section against the second abutment section.

In an embodiment, the force splitter comprises a collet at least partially circumferentially surrounding at least a part of the capillary. The force splitter may further comprise a first ferrule being biased against the collet by the biasing mechanism, wherein the collet and the first ferrule are shaped at mutually abutting surfaces for splitting the fixing force into the advance force component and the clamping force component. Hence, the collet and the first ferrule may have surfaces being slanted with regard to an extension direction of the capillary reception (and particularly may be slanted relative to one another, particularly with slightly different slanting angles further improving the force transmission between the collet and the first ferrule), so that, in view of this simple geometric shaping, the transmitted force will be divided into two vector components. One component will compress the capillary radially and thereby fix it within the fitting, whereas the other component will drive or bias the capillary forwardly (i.e. in direction to the fluidic conduit of the fluidic component) so that an end surface of the capillary will abut or will be pushed against a cooperating sealing surface of the fluidic conduit or the fluidic component, thereby providing for a fluid tight sealing.

In an embodiment, the above mentioned first ferrule is an annular disk with a tapering through hole. The central through hole may receive the capillary and may have an internal through hole diameter which continuously increases towards a free end of the capillary. Therefore, the force splitting may be efficiently performed by the first ferrule in conjunction with the collet.

In an embodiment, the collet is a (for instance slitted) tube with at least one tapering end section. Slitting a tube with one or more circumferential slits extending parallel to a central axis of the capillary reception allows to provide a structure which can be compressed efficiently, for instance crimped or plastically deformed in another way, upon applying a circumferential compression force to the collet. The external surface of the tubular collet may have another diameter which, at least over a part of the extension of the collet, continuously increases from the end of the collet opposing the fluidic component to be connected towards the other end of the collet facing the fluidic component to be connected. Therefore, the force splitting may be efficiently performed by the first ferrule in conjunction with the collet.

In an embodiment, the biasing mechanism is a spring assembly, particularly an assembly of a plurality of plate washers (other types of springs are possible, for instance coil springs or leaf springs). For instance, eight plate washers may be combined, wherein pairs of adjacent plate washers are aligned in parallel to one another with continuous contact surfaces there between. A pair of convex spring washers may be followed by a pair of concave spring washers, and so on, so that a sequence of spring washer pairs of alternating (or opposite) curvature is obtained. Such a plate washer arrangement has the advantage of providing a net force basically in a forward direction, i.e. in an extension direction of the capillary reception. The number of used plate washers as well as the spring constant connected thereto may be selected in accordance with a specific application.

In an embodiment, the fitting further comprises a coupling piece, particularly a coupling disk, arranged between a pivotable eccentric shaft of the force applicator and the biasing mechanism and having a curved coupling surface coupled to the eccentric shaft and a planar coupling surface coupled to the biasing mechanism. Such a coupling piece may be a basically disk-shaped member with a front face which may have a surface perpendicular to an extension of the capillary, whereas a back surface thereof may be curved (particularly in a concave way). Hence, when the eccentric shaft pivots as a result of a user actuation, the eccentric shaft rolls up on the curved surface of the coupling body with a low friction so as to efficiently transfer the actuation force with low losses onto the spring assembly.

In an embodiment, the fitting further comprises a two-piece fitting housing (or a fitting housing having more than two separate pieces) having a first housing piece and a second housing piece, wherein the first housing piece is rotatable relative to the second housing piece when the force applicator is operated to not apply the fixing force, and wherein the first housing piece is fixed relative to the second housing piece when the force applicator is operated to apply the fixing force. With such a two-part housing, it is possible that a user firstly fixes the fluidic component to be coupled with the capillary on the rotatable housing piece, for instance by rotating one of the housing pieces for performing a screwing connection between the fluidic component and one of the housing pieces. Due to the mutually movable adaptation of the two housing pieces relative to one another this fastening procedure is not disturbed by the other housing piece. Upon activating the fixing force by operating the force applicator by a user, the second housing piece may be immobilized relative to the first housing piece, thereby achieving a stable and reproducible configuration.

In an embodiment, the force applicator is pivotably mounted on the first housing piece. More specifically, a pivoting axis of the force applicator may be oriented perpendicular to a rotation direction of the first housing piece relative to the second housing piece.

In an embodiment, the second housing piece has a connection section configured for being connected to a cooperating connection section of the fluidic component. In such a configuration, the second housing piece may for instance form a male part of a connection system, wherein the fluidic component hereby forms the female part. In other words, a front end of the second housing piece may be a protrusion, whereas a back end of the fluidic component may be a recess. However, in another embodiment, this functionality may be inverted. Thus, the second housing piece may alternatively form a female part of a connection system, wherein the fluidic component hereby forms the male part.

In an embodiment, the fitting further comprises a tapering second ferrule at a front end of the fitting and being configured for providing a sealed coupling to the fluidic component. Such a second ferrule may be basically cone shaped with an internal through hole for providing fluid communication from the capillary towards the fluidic conduit to be connected. Hence, the second ferrule may conically taper towards a front end of the fitting, so that a tip thereof may be inserted into a recess of the fluidic component to be connected. Such a second ferrule may be made of a plastic material such as PEEK (Polyetheretherketone) which can be deformed upon application of pressure, thereby providing for a high performance sealing surface even under high pressure conditions (such as in case of modern liquid chromatography applications with pressure values of 1000 bar and more).

In an alternative embodiment, the fitting further comprises a fluidic planar structure reception gap for clampingly receiving a fluidic planar structure as the fluidic component having integrated therein the fluidic conduit. In such an alternative embodiment, an insertion gap may be formed between the two opposing ends of the fitting. Such a gap is configured to insert a fluidic planar structure (which may also be denoted as a fluidic chip) therein for providing a fluid communication between the capillary and an internal fluidic conduit within the fluidic planar structure. The skilled person is aware of the fact that, for instance for liquid chromatography applications, a plurality of layers may be laminated to one another, which layers have been processed beforehand so that an internal fluidic conduit can be formed within this planar or chip-like arrangement. In the present embodiment, the fluidic coupling between such a fluidic conduit of the fluidic planar structure and the capillary may be achieved by a clamping or pressing force which is applied between the fitting and the fluidic planar structure upon actuating the force applicator or force enhancer.

In an embodiment, the fluidic planar structure reception gap is configured for receiving the fluidic planar structure upon inserting the fluidic planar structure along an insertion direction into the gap, which insertion direction may be perpendicular to an extension of the capillary reception. Hence, it is for instance possible that the fluidic planar structure is inserted along a basically vertical insertion direction, whereas an extension of the capillary reception may be basically horizontal. This may ensure for a precise and reliable high pressure connection of the capillary with a fluidic conduit of the planar chip.

In the following, further embodiments of the fluidic device will be explained. However, these embodiments also apply to the fitting and the method.

Fluidic devices according to exemplary embodiments may be particularly suitable for use as fluidic connection pieces for connecting parts of a fluidic instrument such as a liquid chromatographic system or the like. For example, columns, fractioners, detectors, or the like, of a liquid chromatography apparatus may be connected as fluidic components of such a fluidic device.

In an embodiment, at least the part of the capillary being received in the capillary reception is at least partially circumferentially covered by a sleeve. Such a tubular sleeve may locally thicken the capillary and may be made of a metallic structure which is pressed onto the capillary, for instance by crimping, so that it covers the entire perimeter of the capillary.

In an embodiment, the fluidic component is a fluidic planar structure which comprises a plurality of laminated sheets being patterned so as to form the fluidic conduit for conducting the fluidic sample integrated in the layer sequence. Thus, the fitting may provide a connection between a conventional capillary system and a planar fluidic chip device which may have a chromatographic column integrated therein.

In an embodiment, the fluidic component is a processing element configured for processing the fluidic sample. Thus, such a processing element may process the fluid, for instance separate it, purify it, apply a tempering step, or the like.

Particularly, the processing element may be a chromatographic separation column which may separate different fractions of a fluidic sample due to a different affinity of the various fluidic fractions to a stationary phase of the separation column. For instance, by applying a gradient run, the trapped fractions may be released from the separation column individually, thereby separating them.

The fluidic device may comprise a processing element filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluoroethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The fluidic device may be configured as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the fluidic device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and analyzed.

The fluidic device may be configured to conduct the mobile phase through the system with a high pressure, particularly of at least 600 bar, more particularly of at least 1200 bar (for instance up to 2000 bar).

The fluidic device may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less (for instance down to 15 µm or 12 µm). The analysis system may also be configured as a nanofluidic device. The term "nanofluidic device" may particularly denote a fluidic device as described herein which allows to convey fluid through nanochannels with a flow rate of less than 100 nl/min, particularly of less than 10 nl/min.

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs.

Figure 1:
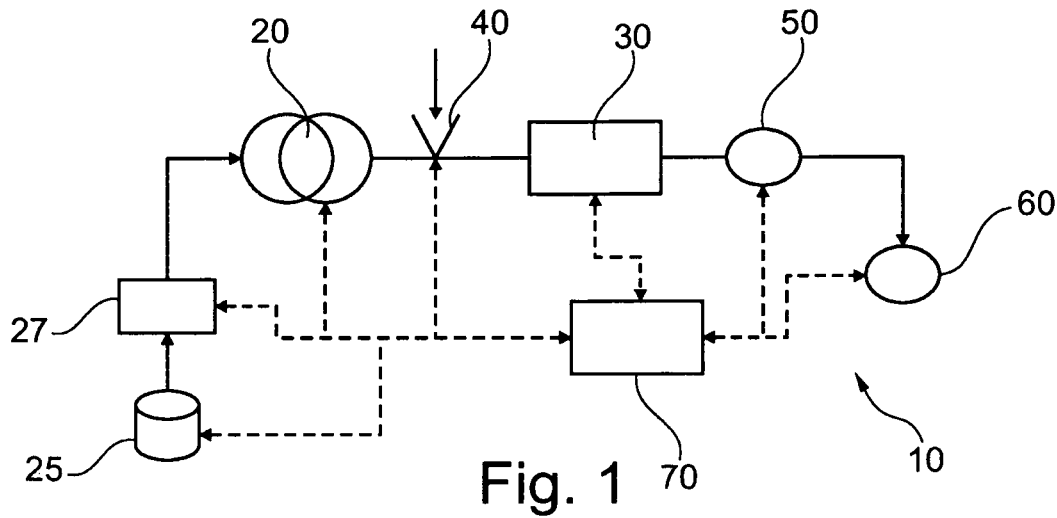
FIG. 1 shows a liquid separation device in accordance with embodiments of the present invention, particularly used in high performance liquid chromatography (HPLC).

The illustration in the drawing is schematic.

Referring now in greater detail to the drawings, FIG. 1 depicts a general schematic of a liquid separation system 10. A pump 20 receives a mobile phase from a solvent supply 25, typically via a degasser 27, which degasses and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device

30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump 20). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization of sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provide data back.

From the example of FIG. 1, it can be seen that the flow path of the mobile phase typically comprises plural individual components, such as pump 20, separating device 30, sampling unit 40, and detector 50, which are coupled together and which might also be comprised of individual sub-components. Also, fluid conduits, e.g. capillaries, for conducting the fluid are provided as indicated by the solid connections in FIG. 1. Coupling of parts, components and fluid conduits, in particular when using exchangeable or modular parts, is usually provided by using fittings.

For transporting liquid within the liquid separation system 10, typically tubings (e.g. tubular capillaries) are used as conduits for conducting the liquid. Fittings are commonly used to couple plural tubings with each other or for coupling a fluid conduit (e.g. a tubing) to any device. For example, fittings can be used to connect respective fluid conduit to an inlet and an outlet of the chromatographic column 30 in a liquid-sealed fashion. Any of the components in the fluid path (solid line) in FIG. 1 may be connected by fluid conduits e.g. using fittings. While the fluid path after the column 30 is usually at lower pressure, e.g. 50 bar or below, the fluid path from the pump 20 to the inlet of the column 30 is under high pressure, currently up to 1200 bar, thus posing high requirements to fluid tight connections.

Due to the high pressure applied in most HPLC applications, pressure sealing of the components in and along the flow path is required. Further, in case of requirement of biocompatibility, it has to be ensured that all surfaces of components (including conduits) along the flow path, which may come in contact with the mobile phase and the sample fluid, are comprised of materials generally considered as being biocompatible, i.e. not releasing ions (e.g. from metal parts) which may contaminate the sample and/or a column packaging material, and/or adversely affect the analysis itself. Accordingly, proper sealing is required to ensure such biocompatibility.

Figure 2:
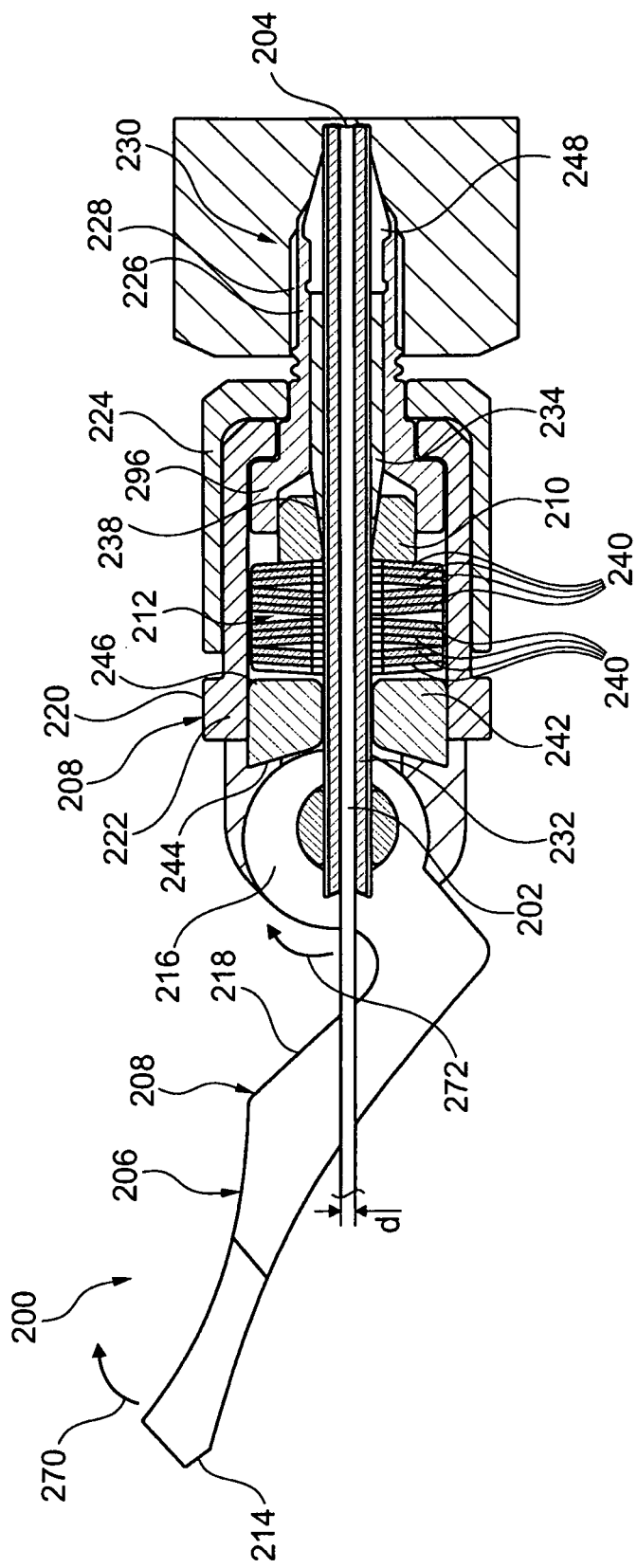
FIG. 2 illustrates a fitting for providing a fluid connection between a capillary and a fluidic conduit of a separation column according to an exemplary embodiment of the invention.

FIG. 2 illustrates a fitting 200 for providing a fluid connection between a capillary 202 and a fluidic conduit 204 (only indicated partially and schematically in FIG. 2) of a fluidic component 230 according to an exemplary embodiment of the invention.

The fitting 200 can be used for multiple purposes, but particularly for providing a high pressure sealing connection between the capillary 202 (having an internal fluid conducting lumen) on the one hand and a capillary or the like forming the fluidic conduit 204 of the fluidic component 230 on the other hand. The fluidic component 230 can be a chromatographic separation column, as the one denoted with reference numeral 30 in FIG. 1.

In the following, the construction of the fitting 200 will be explained in more detail. The fitting 200 comprises a housing which is constituted of different housing parts, such as those denoted with reference numerals 222 and 224 in FIG. 2. The housing has, as an interior recess thereof, a capillary reception volume which is shaped and dimensioned as a central basically cylindrical recess and which is configured for receiving and accommodating the capillary 202. The capillary 202 has a portion which is shown in FIG. 2 outside of the fitting 200 and which may be free of any further cover layers. However, another section of the capillary 202 being accommodated within the fitting 200 can be surrounded by an optional metallic sleeve 232. The capillary 202, covered by the sleeve 232 along a subsection thereof, can be inserted by a user in the capillary reception by a sliding motion along a horizontal direction of FIG. 2 from a left hand side to a right hand side.

A force applicator 206, in the shown embodiment also acting as a force enhancer, is provided and configured for being operable to apply a fixing force for fixing the capillary 202 received within the capillary reception volume of the fitting 200. Hence, by a user operating the force applicator 206, the capillary 202 may be clamped in the capillary reception so that it cannot be removed from the fitting 200 in the clamped state.

Beyond this, a force limitation mechanism 208 is provided and configured for limiting the fixing force amplitude of the fixing force which is applicable by the force applicator 206 to the capillary 202. In other words, the force limitation mechanism 208, as described below in more detail, ensures that the fixing force applied to the capillary 202 will never exceed a predefined maximum fixing force. Thus, the capillary 202 may be prevented from any deterioration due to a too high force acting thereon.

Moreover, a force splitter 210, 234 is a mechanism which is configured for splitting the fixing force into two components. The first component is an advance force component which has the tendency of advancing the capillary 202 received in the capillary reception forwardly towards the first component, i.e. towards a right hand side of FIG. 2. A second component of the applied fixing force split by the force splitter 210, 234, is a clamping force component which clamps the capillary 202 received in the capillary reception within the fitting 200. This clamping force is directed circumferentially inwardly, i.e. is applied towards a full circumference of the capillary 202.

Furthermore, a biasing mechanism 212 is provided. As can be taken from FIG. 2, the biasing mechanism 212 is an assembly of eight plate washers 240, i.e. four concave plate washers and four convex plate washers, which are arranged in a pairwise alternating way so as to form the spring package shown in FIG. 2. The biasing mechanism 212 is arranged between the force applicator 206 and the force splitter 210, 234 (but may be located elsewhere). It may be configured for biasing a force splitter 210, 234 against the capillary. In other words, a biasing force may be applied from the biasing mechanism which promotes a forward motion of the capillary 202, i.e. towards the fluidic conduit 204 to be connected thereto. This ensures a proper sealing at an interface between capillary 202 and fluidic conduit 204. Furthermore, in case of a reduction or loss of a forward pressing force which presses the capillary 202 against the fluidic conduit 204, for example due to ageing effects or temperature induced effects, the biasing mechanism may deliver an additional force which maintains the sealed coupling between fluidic component 230 and capillary 202. Furthermore, this additionally promotes a clamping of the capillary 202 within the fitting 200 so that the biasing mechanism can also prevent an undesired sliding of the capillary 202 within the fitting 200.

As can be taken from FIG. 2, the force applicator 206 has a lever 214 which is manually operable by a user. For this purpose, the lever 214 is anatomically shaped to be grippable by a hand of the human being. The force applicator 206 furthermore has an eccentric shaft 216 having a shaft axis which is arranged perpendicular to the paper plane of FIG. 2. Eccentric shaft 216 is rigidly coupled to the lever 214, i.e. is integrally formed therewith from a metallic material or the like, so that pivoting the lever 214 pushes the eccentric shaft 216 towards biasing mechanism 212 to thereby apply the fixing force. Due to the eccentric mounting of the force applicator 206 at the casing or housing of the fitting 200, a rotation of the lever 214 in a direction as indicated by an arrow 270 in FIG. 2 also results in a rotation of the eccentric shaft 216, as indicated by an arrow 272. Due to the eccentric assembly, the force applied by the eccentric shaft 216 forwardly, i.e. towards the right hand side end of the capillary 202, is continuously increased with increasing pivoting angle. Since the lever 214 is manually operable by a user without the need of using a specific tool, handling of the fitting 200 is very user convenient.

As mentioned above, pivoting the lever 214 continuously increases the fixing force applied from the force applicator 206 onto the capillary 200, transmitted by various intermediate components as described below in more detail. However, the fitting 200 has a mechanism of preventing that the applied force exceeds a maximum value which is adjusted so that the application of the force does not deteriorate the capillary 202. For this purpose, the force limitation mechanism has a first abutment member 218 which is a surface portion of the force applicator 206 which approaches a corresponding second abutment member 220 of the housing 222 (a surface thereof) with continued rotation of the force applicator 206. Hence, the second abutment member 220 forms part of the fitting housing 222. More precisely, the second abutment member 220 is a surface portion of a corresponding housing part 222 which projects or protrudes so as to be selectably brought in contact with the first abutment member 218 when the lever 214 has been rotated until it comes in contact with the housing part 222. This abutment inhibits a further continued operation of the force applicator 206, thereby inhibiting exceeding of the fixing force. When the abutment members 218, 220 abut against one another, further continued rotation of the lever 240 along arrow 270 is rendered impossible, thereby disabling a further increase of the fixing force.

The above mentioned force splitter mechanism 210, 234 is realized in the shown embodiment of the fitting 200 in particular by the cooperation of two components: collet 234 and first ferrule 210. The collet 234 circumferentially surrounds the entire capillary 202. The first ferrule 210 is biased against the collet 234 by a biasing force exerted by biasing mechanism 212. The collet 234 and the first ferrule 210 are shaped to have corresponding abutting surfaces 238. These are slanted relative to an extension direction of the capillary 202 (the extension direction is a horizontal direction according to FIG. 2) for splitting the fixing force into the longitudinal advance force component and the circumferential and inwardly directed clamping force component. The first ferrule 210 is configured as an annular disk with a tapering through hole. The through hole of the first ferrule 210 has an inner diameter at an interface to the biasing element 210 which is smaller than an inner diameter of the first ferrule 210 at an interface facing the fluidic component 230. In view of the described geometry, the force applied by the force applicator 206 is divided into two vector components, one compressing the capillary 202 and the other one pressing or pushing the capillary 202 towards the right hand side of FIG. 2.

As can be taken from FIG. 2, the collet 234 may be configured as a longitudinally slitted tube with a tapering end section (the one on the left hand side of FIG. 2). In other words, the end section of the collet 234 contacting the first ferrule 210 is slanted as well, to ensure a proper force transmission. To match the tapering of the first ferrule 210, the end section of the collet 234 increases its diameter from the left hand side of FIG. 2 to the right hand side of FIG. 2. The slanting angles of the collet 234 and of the first ferrule 210 may be the same or may be slightly different (for instance may differ by an angle in a range between 1° and 10°), wherein a slight difference in the slanting angle may improve the force transmission between the collet 234 and the first ferrule 210.

A coupling piece 242 is arranged as a separate member between the pivotable eccentric shaft 216 of the force applicator 206 on the one hand and the biasing mechanism 212 on the other hand. The coupling piece 242 has a concavely curved coupling surface 244 contacting and cooperating with the eccentric shaft 216. Opposing to the curved coupling surface 244, the coupling piece 242 has a planar coupling surface 246 which contacts and cooperates with the biasing mechanism 212. The coupling piece 242 is also embodied as an annular member, i.e. a basically cylindrical member with an internal through hole. Upon pivoting the lever 214, an external cylindrical surface of the eccentric shaft 216 performs a rolling motion on the concave curved surface 244 of the coupling piece 242.

FIG. 2 furthermore shows that the above mentioned housing is constituted as a multiple piece housing having a first housing piece 222 and a second housing piece 224. The first housing piece 222 is rotatable relative to the second housing piece 224 in the absence of a fixing force applied by the force applicator 206. In other words, in an operation mode as shown in FIG. 2 in which no fixing force is applied to the force applicator 206 towards a capillary 202, the first housing piece 222 can be rotated relative to the second housing piece 224, for instance by holding one of the housing pieces 222, 224 and pivoting down on one 224 or 222. Moreover, the first housing piece 222 is fixed relative to the second housing piece 224 when the force applicator 206 is operated to apply the fixing force. Thus, the pivoting of the force applicator 206 not only applies a fixing force of the capillary 200 but also ensures to selectively immobilize or mobilize the housing pieces 222, 224 relative to one another.

It is possible to provide a connection element 296 (mounted in the housing pieces 222, 224) of the fitting 200 with an external thread 226. The latter may be configured for being connectable to a cooperating internal thread 228 of the fluidic component 230. Therefore, the fluidic component 230 may be connected to the fitting 200 by screwing, i.e. by rotating the second housing piece 224 relative to the fluidic component 230, wherein the first housing piece 222 can be disabled from following this rotation when the force applicator 206 is not in its fixed but in its released state. Therefore, it is advantageous for a described screwing connection that the two housing pieces 222, 224 are rotatable relative to one another.

After this screwing operation, rotation of the pivoting lever 214 not only fixes the capillary 200 in a sealed way within the cavity reception of the fitting 200, but simultaneously disables undesired rotation between housing parts 222, 224.

An arrow-shaped tapering second ferrule 248 is provided as a further part of the fitting 200. It is arranged in a front end of the fitting 200 and is configured for providing a sealed coupling to the fluidic component 230. The tapering second ferrule 248 is shaped, in the shown embodiment, as a hollow cone-like member of a material (such as PEEK or any other appropriate plastic material) which deforms upon applying pressure, thereby contributing significantly to the sealing between fitting 200 and fluidic component 230.

For operating the fitting 200, a screwing connection between the cooperating threads 226, 228 may be formed. A user may guide the capillary 202 through the capillary reception of the fitting 200 until it abuts through the fluidic conduit 204 to which it is to be fluidically connected. Subsequently, the lever 214 may be pivoted as to apply the fixing force exerted onto the capillary 202 in a forward and a circumferential direction as well. Simultaneously, this pivoting disables rotation between housing parts 222, 224.

The capillary 202 may be made of a flexible material (for instance a plastic material or a metallic material such as steel). For example, an outer diameter d of the capillary 202 may be 1.6 mm. The sleeve 232 (which can also be denoted as a socket) may be slid onto the capillary 202 and may be welded to the capillary 202, for instance by laser welding. The biasing mechanism 212 is an active member for providing a sealing force independently of temperature effects or aging effects. The plate washers 240 of the biasing mechanism 212 can be made of steel which may be harder than capillary steel. Housing part 224 may be a knurl sleeve being freely rotatable when the lever 214 is in the open state of FIG. 2. When the lever is closed (not shown) the knurl sleeve is fixed at the housing part 222. The first ferrule 210 compresses the collet 234 so that the capillary 202 can be clamped in place circumferentially. The force applicator 206 and the coupling piece 242 may be made of the same material, for instance steel. With the shown force application mechanism, a muscle force of 30 N may be enough to obtain a holding force or fixing force of 800 N. An overload protection preventing a too high force to be applied to the capillary 202 is provided by the force limitation mechanism 208 and also by the spring packet 212.

The force transmission is performed from the lever 214 to the pressure disk or coupling piece 242, from the coupling piece 242 to the spring packet 212, and from the spring packet 212 to the back ferrule 210. Due to the corresponding shaping of back ferrule 210 and the slitted collet 234, the back ferrule 210 presses the collet 234 inwardly. At the same time, the back ferrule 210 presses the collet 234 forwardly, i.e. towards the direction of the front ferrule 248.

In the following, several advantageous properties of the fitting 200 according to an exemplary embodiment of the invention are summarized: The fitting 200 is high pressure-resistant up to 2,000 bar which corresponds to 400 N sealing force at a 25 μm capillary. Compensation of the pressure and temperature fluctuations caused by springs 240 is performed. A force amplifier function is fulfilled by an eccentric lever mechanism. Hence, a manual force of only about 25 N is sufficient. It is possible to orient the lever 214 by decoupling. The fitting 200 has an overload protection, is tool-free operable and is easy to use. It has replaceable wear parts. The fitting 200 has a long lifetime because of its exclusively linear motion. Hence, there is no stress or torsion. The fitting 200 is fully compatible with standard column connections. It has a releasable connection.

An applied hand force on the lever 214 results in a clamping force of 800 N (corresponding to 3,600 bar pressure). This corresponds to an amplification of factor 32. The clamping force is applied to the spring assembly or biasing mechanism 212, which acts as overload protection and compensator. This spring package subsequently pushes back ferrule 210, which compresses the collet 234. Through the compressed collet 234, the capillary 202 is kept and in addition pressed forward to the column port. Sealing is accomplished with the ferrule 248 on PEEK base.

Figure 3:
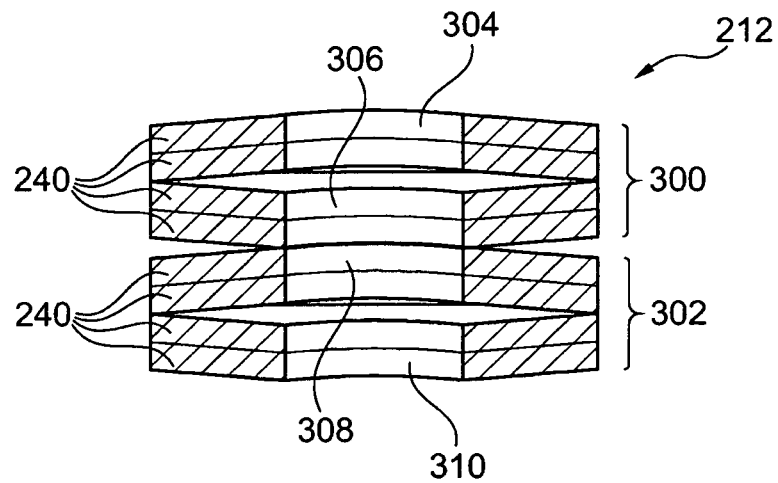
FIG. 3 shows a spring packet implemented in the fitting of FIG. 2.

FIG. 3 shows the arrangement of the plate washers 240 forming the biasing assembly 212 in detail. As can be taken from FIG. 3, the eight spring washers 240 used in this embodiment are grouped to four groups of adjacent spring pairs, wherein concave spring pairs and convex spring pairs alternate along an extension of the spring packet shown in FIG. 3.

Figure 4:
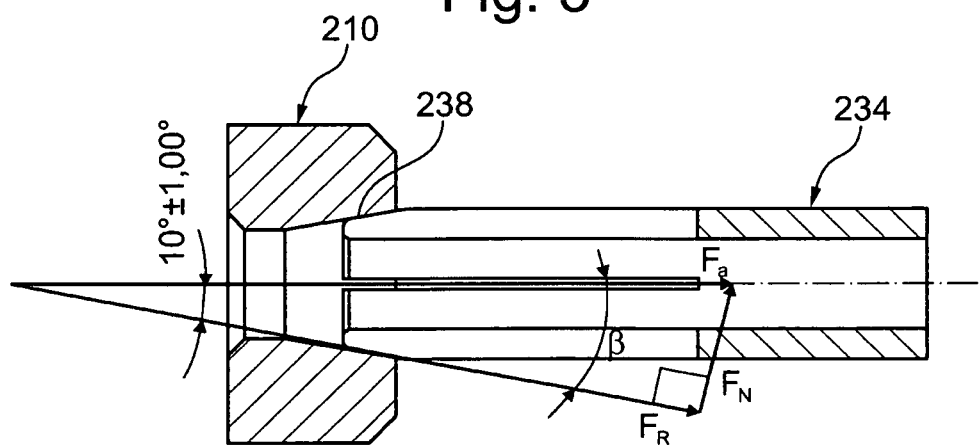
FIG. 4 illustrates the geometry of a force transmission along a horizontal direction of FIG. 2.

FIG. 4 illustrates a force transmission to the back ferrule 210 and from there to the collet 234 (subsequently to the capillary 202). Depending on the wedge angle β which is a design parameter when embodying a fitting 200, the applied actual loading force $F_a$ has a normal component $F_n$ and a tension force component $F_r$.

Figure 5:
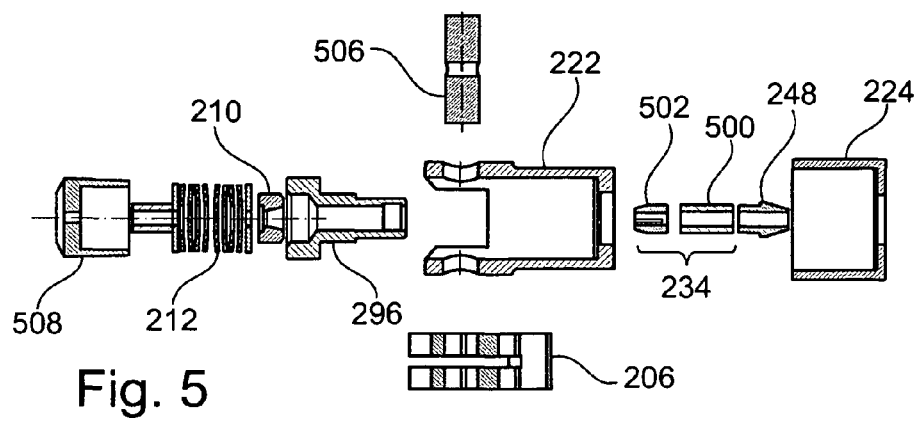
FIG. 5 shows an exploded view of a fitting according to an exemplary embodiment of the invention.

FIG. 5 shows an exploded view of a fitting according to an exemplary embodiment of the invention. The shown fitting is appropriate for the use with capillary connection systems. Spring packet 212 serves as a pressure and temperature balancing element as well as for overload protection. As high pressure sealing and capillary holders, a socket 500, a clamping cone 248 and a tapering piece 502 are foreseen. Reference numerals 500 and 502 form collet 234. Also back ferrule 210 contributes to the function of a high pressure sealing and capillary holders.

Hollow screw or connection element 296 serves as a connector to the separation column via a corresponding thread 226. Eccenter lever 206 is fixed to the eccentric housing part 222 by means of shaft 506. The eccentric housing part 222 also serves as a coupling nut for the connection element 296. Together with a pressure disk 508, a clamping force is transmitted to the spring packet 212 and then to the back ferrule 210 to be accommodated in the connection element 296. Alignment may be performed in an open state by pivoting the knurl sleeve or housing part 224 while maintaining the eccentric housing part 222 spatially fixed.

Figure 6:
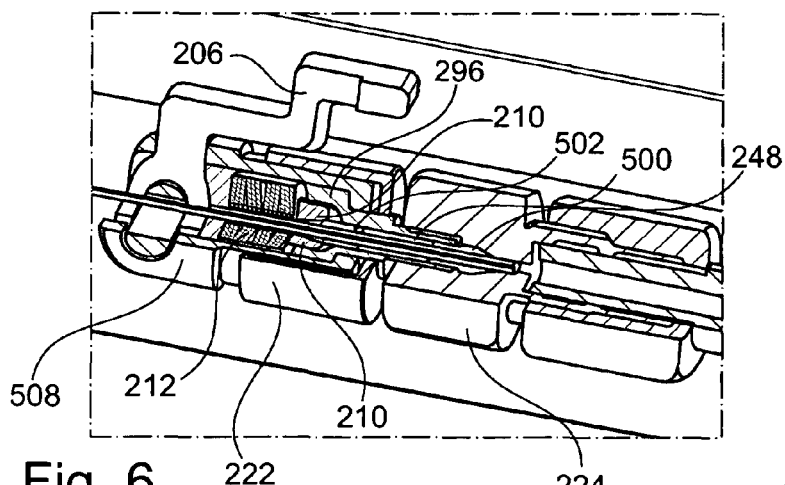
FIG. 6 shows the fitting of FIG. 5 in an assembled cross-sectional view.

FIG. 6 shows the fitting of FIG. 5 in an assembled state.

Figure 7:
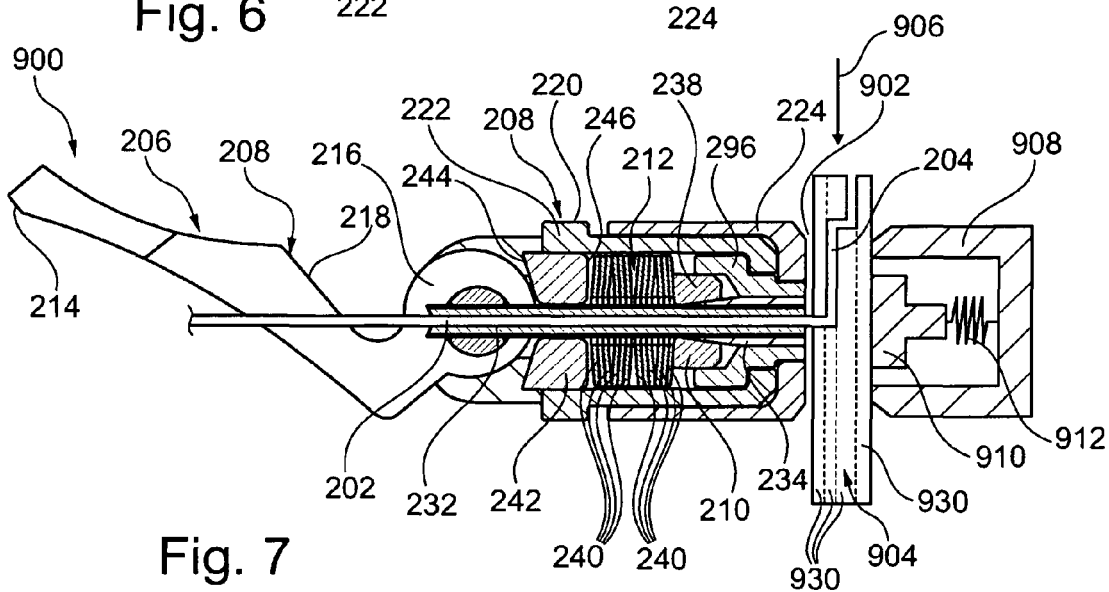
FIG. 7 illustrates a fitting for providing a fluid connection between a capillary and a fluidic conduit of a planar chip device according to an exemplary embodiment of the invention.

FIG. 7 shows a fitting 900 according to still another exemplary embodiment of the invention. Many of the components shown in FIG. 7 are similar or identical to those shown in FIG. 2. However, the differences between FIG. 2 and FIG. 7 will be described in the following in more detail.

A main difference between the embodiment of FIG. 7 and the embodiment of FIG. 2 is that with the embodiment of FIG. 7, the capillary 202 is not connected to a conventional chromatographic separation column 230, but in contrast with this with a fluidic channel 204 formed in a fluidic planar structure 904 which is made from a number of thin sheets 930 (of plastic or metal) laminated together and processed so as to have internal grooves. In combination, the grooves form fluidic channel 204. For mounting the fluidic planar structure 904, the fitting 900 has a fluidic planar structure reception cap 902 which is configured for clampingly receiving the fluidic planar structure 904 as a fluidic component having integrated therein the fluidic conduit 204 and to be fluidically coupled to the capillary 202. The fluidic planar structure reception gap 902 is configured for receiving the fluidic planar structure 904 when the latter is longitudinally shifted along an insertion direction 906 which is perpendicular to an extension direction of the capillary 202 and the capillary reception.

A counter piece housing part 908 is provided as well which presses from a right hand side against the fluidic planar structure 904 when being inserted in the fluidic planar structure reception gap 902. A plunger 910 presses the chip 904 towards an opposing surface of the housing piece 224. The plunger 910 is biased to a left hand side via a spring 912 mounted between the plunger 910 and the counter piece housing 908.

In operation, the fluidic planar structure 904 is inserted in the fluidic planar structure reception cap 902. It will then be pressed by the biasing force of the spring 912 and by means of the plunger 910 towards the left hand side of the fluidic planar structure reception gap 902, i.e. will sealingly abut on the surface of the housing piece 224. Upon pivoting the lever 214 after having inserted the capillary 202 into a capillary reception, the capillary 202 is fixed within the fitting 900 and will at the same time be sealingly forced to abut to an end of the fluidic channel 204 integrated in the multilayer laminated microfluidic planar structure 904.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A fitting for providing a fluid connection between a capillary and a fluidic conduit of a fluidic component, the fitting comprising:

a fitting housing comprising a housing end with an opening;

a force applicator configured for applying a fixing force for fixing the capillary within the fitting, the force applicator comprising a shaft connecting the force applicator to the fitting housing for pivoting the force applicator relative to the fitting housing, wherein the capillary is disposed through the opening;

a force limitation mechanism configured for limiting the fixing force being applicable by the force applicator to the capillary;

a force splitter configured for splitting the fixing force into an advance force component for advancing the capillary towards the fluidic component and into a clamping force component for clamping the capillary within the fitting;

a biasing mechanism arranged between the force applicator and the force splitter, and the biasing mechanism disposed between the housing end and the force splitter, the biasing mechanism configured for biasing the force splitter against the capillary; and a coupling piece arranged as a separate member between the shaft and the biasing mechanism.

2. The fitting according to the claim 1, wherein the force applicator has a lever operable by a user.

3. The fitting according to the claim 2, wherein the shaft comprises an eccentric shaft rigidly coupled to the lever so that pivoting the lever pushes the eccentric shaft towards the biasing mechanism to thereby apply the fixing force.

4. The fitting according to claim 1, wherein the force limitation mechanism has a first abutment member forming part of the force applicator and has a second abutment member forming part of a fitting housing, wherein the first abutment member and the second abutment member are configured so as to abut to one another for inhibiting continued operation of the force applicator thereby inhibiting exceeding of the fixing force.

5. The fitting according to claim 1, wherein the force splitter comprises a collet at least partially circumferentially surrounding at least a part of the capillary and comprises a first ferrule being biased against the collet by the biasing mechanism, wherein the collet and the first ferrule are shaped at mutual abutting surfaces so as to be slanted relative to an extension direction of the capillary, for splitting the fixing force into the advance force component and the clamping force component.

6. The fitting according to claim 5, wherein the first ferrule is an annular disk with a tapering through hole.

7. The fitting according to claim 5, wherein the collet is a slitted tube with a tapering end section.

8. The fitting according to claim 1, wherein the biasing mechanism is selected from the group consisting of: a spring assembly, a spring assembly comprising a plurality of plate washers, and a spring assembly comprising one or more concave plate washers and one or more convex plate washers.

9. The fitting according to claim 1, wherein the shaft is a pivotable eccentric shaft, and the fitting further comprises a coupling piece arranged between flail the pivotable eccentric shaft of the force applicator and the biasing mechanism and having a curved coupling surface coupled to the eccentric shaft and a planar coupling surface coupled to the biasing mechanism.

10. The fitting according to claim 1, wherein the fitting housing comprises a first housing piece and a second housing piece, the first housing piece is rotatable relative to the second housing piece in the absence of a fixing force applied by the force applicator, and the first housing piece is fixed relative to the second housing piece when the force applicator is operated to apply the fixing force.

11. The fitting according to claim 10, wherein the second housing piece has a connection section, particularly an external screw, configured for being connected to a cooperating connection section, particularly an internal screw, of the fluidic component.

12. The fitting according to claim 1, further comprising a fluidic planar structure reception gap configured for clampingly receiving a fluidic planar structure as the fluidic component having integrated therein the fluidic conduit.

13. The fitting according to claim 12, wherein the fluidic planar structure reception gap is configured for receiving the fluidic planar structure in an insertion direction which is perpendicular to an extension direction of the capillary reception.

14. A fluidic device for conducting a fluidic sample, the fluidic device comprising:
  a fluidic component having a fluidic conduit;
  a capillary; and
  a fitting according to claim 1 for providing a fluid connection between the capillary when received in the fitting and the fluidic conduit of the fluidic component when connected to the fitting for conducting the fluidic sample through the fluidic device.

15. The fitting according to claim 1, wherein the force applicator is positioned proximate to the housing end.

16. The fitting according to claim 1, wherein the biasing mechanism is configured for receiving the capillary therethrough such that the capillary is insertable from the housing end into the capillary reception, through the biasing mechanism, and into the force splitter.

17. A method of fluidically coupling a capillary with a fluidic conduit of a fluidic component by a fitting having a fitting housing, the method comprising:
  receiving the capillary in an opening of a housing end of the fitting housing;
  operating a force applicator of the fitting to apply a fixing force for fixing the capillary within the fitting, the force applicator comprising a shaft connecting the force applicator to the fitting housing for pivoting the force applicator relative to the fitting housing, wherein the capillary is disposed through the opening;
  limiting the fixing force being applicable by the force applicator to the capillary by a force limitation mechanism of the fitting;
  splitting the fixing force, by a force splitter of the fitting, into an advance force component for advancing the capillary towards the fluidic component and into a clamping force component for clamping the capillary within the fitting; and
  biasing the force splitter against the capillary by a biasing mechanism of the fitting, the biasing mechanism arranged between the force applicator and the force splitter, and the biasing mechanism disposed between the housing end and the force splitter,
  wherein the fitting has a coupling piece arranged as a separate member between the shaft and the biasing mechanism.

18. The method according to claim 17, comprising receiving the capillary such that the capillary is inserted into the force splitter via the biasing mechanism.

* * * * *